(12) United States Patent
Suddaby

(10) Patent No.: US 7,591,840 B2
(45) Date of Patent: Sep. 22, 2009

(54) ORTHOPEDIC FUSION PLATE HAVING BOTH ACTIVE AND PASSIVE SUBSIDENCE CONTROLLING FEATURES

(76) Inventor: Loubert Suddaby, 76 Tanglewood Dr., Orchard Park, NY (US) 14127

( * ) Notice: Subject to any disclaimer, the term of this patent is extended or adjusted under 35 U.S.C. 154(b) by 0 days.

(21) Appl. No.: 11/337,073

(22) Filed: Jan. 23, 2006

(65) Prior Publication Data
US 2006/0167457 A1    Jul. 27, 2006

Related U.S. Application Data

(60) Provisional application No. 60/645,044, filed on Jan. 21, 2005.

(51) Int. Cl.
*A61B 17/66* (2006.01)
(52) U.S. Cl. .............. 606/282; 606/70; 606/71
(58) Field of Classification Search ............. 606/69–71, 606/105, 282, 280, 283, 284
See application file for complete search history.

(56) References Cited

U.S. PATENT DOCUMENTS

| | | | |
|---|---|---|---|
| 2,486,303 A | 10/1949 | Longfellow | |
| 5,324,290 A | 6/1994 | Zdeblick et al. | |
| 5,616,142 A | 4/1997 | Yuan et al. | |
| 6,224,602 B1 | 5/2001 | Hayes | |
| 6,280,445 B1* | 8/2001 | Morrison et al. | 606/61 |
| 6,402,756 B1 | 6/2002 | Ralph et al. | |
| 6,503,250 B2 | 1/2003 | Paul | |
| 6,652,525 B1 | 11/2003 | Assaker et al. | |
| 6,666,867 B2 | 12/2003 | Ralph et al. | |
| 6,679,887 B2 | 1/2004 | Nicholson et al. | |
| 6,689,134 B2 | 2/2004 | Ralph et al. | |
| 6,695,846 B2 | 2/2004 | Richelsoph et al. | |
| 6,755,833 B1 | 6/2004 | Paul et al. | |
| 2002/0065517 A1 | 5/2002 | Paul | |
| 2002/0111630 A1 | 8/2002 | Ralph et al. | |
| 2003/0149434 A1 | 8/2003 | Paul | |
| 2003/0153920 A1 | 8/2003 | Ralph et al. | |
| 2003/0212399 A1 | 11/2003 | Dinh et al. | |
| 2004/0106924 A1 | 6/2004 | Ralph et al. | |
| 2004/0181226 A1 | 9/2004 | Michelson | |
| 2004/0204713 A1 | 10/2004 | Abdou | |
| 2004/0220571 A1 | 11/2004 | Assaker et al. | |
| 2005/0004573 A1 | 1/2005 | Abdou | |
| 2005/0010227 A1 | 1/2005 | Paul | |
| 2005/0043732 A1* | 2/2005 | Dalton | 606/61 |

* cited by examiner

*Primary Examiner*—Thomas C Barrett
*Assistant Examiner*—Andrew Yang
(74) *Attorney, Agent, or Firm*—Shoemaker and Mattare

(57) ABSTRACT

An orthopedic fusion plate device has a rigid perimetral frame which embraces a pair of plates retained within the frame by a tongue and groove mechanism so that the plates can move in only a single dimension, toward and away from another. The device is intended to mitigate the effects of bone graft resorption and settling through either active or passive mechanisms.

4 Claims, 4 Drawing Sheets

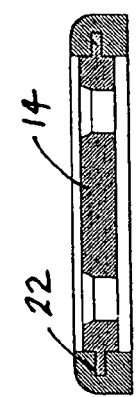
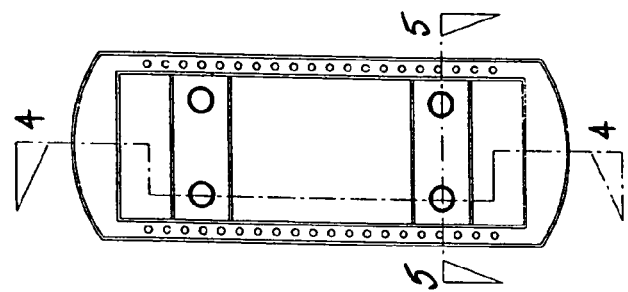
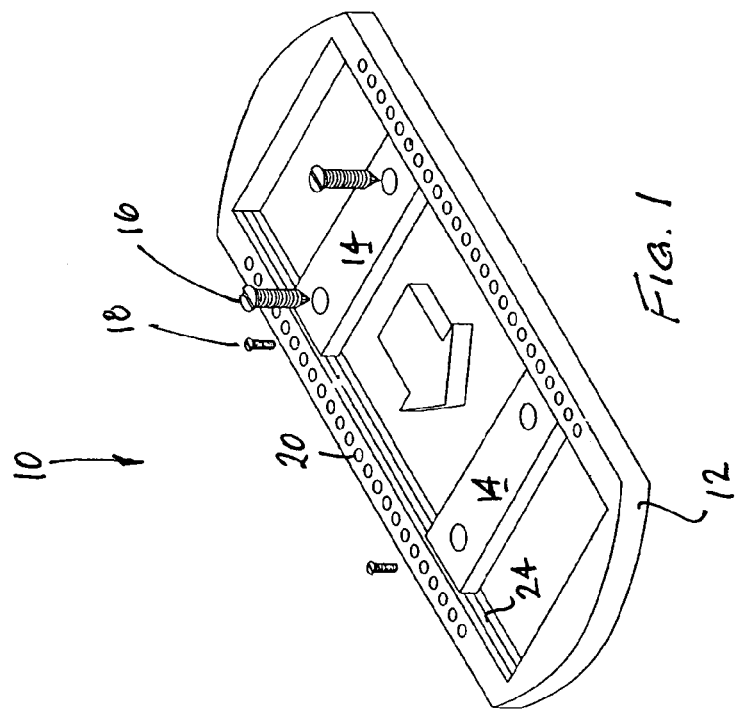

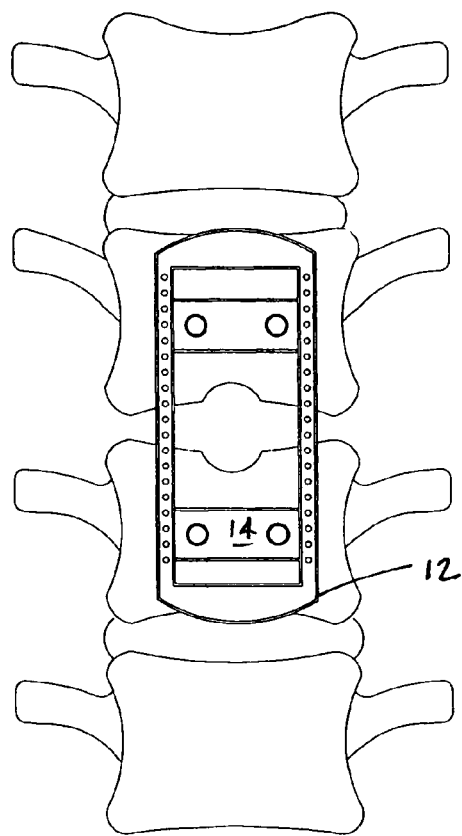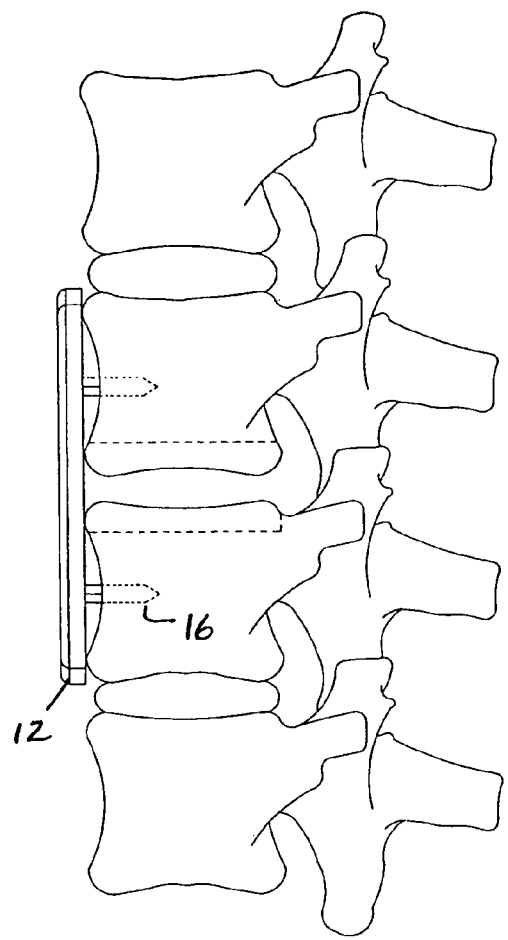
FIG. 6
FIG. 7

ORTHOPEDIC FUSION PLATE HAVING BOTH ACTIVE AND PASSIVE SUBSIDENCE CONTROLLING FEATURES

This application claims benefit under 35 USC 119(e) from provisional patent application 60/645,044, filed Jan. 21, 2005.

BACKGROUND OF THE INVENTION

This invention relates to orthopedic surgery and more particularly to orthopedic fusion plates designed for rigid and semirigid fixation to encourage bony union when bone grafts are used in spinal fusion techniques.

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have the horizontal backbones of other animals. As a result, stresses acting upon the human backbone (or vertebral column) are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, and five bones in the low back or lumbar region. There are also five bones in the pelvic or sacral region which are normally fused together and form the back part of the pelvis. This column of bones is critical for protecting the delicate spinal cord and nerves, and for providing structural support for the entire body.

Between the vertebral bones themselves exist soft tissue structures-discs—composed of fibrous tissue and cartilage which are compressible and act as shock absorbers for sudden downward forces on the upright column. The discs allow the bones to move independent of each other, as well. The repetitive forces which act on intervertebral discs during repetitive day-to-day activities of bending, lifting and twisting cause them to break down or degenerate over time.

Presumably because of humans upright posture, their intervertebral discs have a high propensity to degenerate. Overt trauma, or covert trauma occurring in the course of repetitive activities disproportionately affect the more highly mobile areas of the spine. Disruption of a discs internal architecture leads to bulging, herniation or protrusion of pieces of the disc and eventual disc space collapse. Resulting mechanical and even chemical irritation of surrounding neural elements (spinal cord and nerves) cause pain, attended by varying degrees of disability. In addition, loss of disc space height reduces tension on the longitudinal spine ligaments, thereby contributing to spinal instabilities such as spinal curvature and lithesis.

The time honored method of addressing neural irritation and instability resulting from severe disc damage have largely focused on removal of the damaged disc and fusing the adjacent vertebral elements together. Removal of the disc relieves the mechanical and chemical irritation of neural elements, while osseous union (bone knitting) solves the problem of instability.

In the cervical spine, the most common type of fusion utilizes either bone dowels (Cloward Technique) or bone blocks (Smith Robinson Technique). These procedures have been used now for over four decades. One of the main causes of failure of these fusion techniques is the failure to fuse, or non-union, at the site where the bone is grafted between the vertebral bodies. In an attempt to circumvent this problem, various plate-type mechanism have been used both to provide instability, and to reduce or eliminate movement at the site of the fusion to allow successful bone knitting. These plating mechanisms function much as a cast on a fractured limb might provide support until healing can occur.

It is recognized that for bone knitting to occur, the interfaces of bone required to knit or heal must be held in close apposition and motion between the knitting or fusion interfaces must be restricted sufficiently for a certain minimal time period to permit stable bone union occur.

To achieve these ends, prior inventors have developed a variety of both external braces and internal fixation instruments, some in the form of plates. Internal fixation is advantageous in that it obviates the need for cumbersome external braces, collars or supports and ensures essentially total compliance. U.S. Pat. Nos. 5,041,113, 5,234,431, 5,344,421 and 5,681,311 provide examples of prior vertebral bone plate systems. U.S. Pat. No. 3,604,414 discloses a plate for setting fractures having separate elements which are attached to respective bone fragments and have a toothed interface to maintain the position of the fragments after they have been drawn together.

While interface apposition and retardation of motion are known to enhance bone healing, it is also recognized that if the bony surfaces to be fused are held together under a compression force, osseous fusion is further enhanced.

Even though many plating systems place bone grafts under sufficient compression to facilitate or even enhance bony fusion, bone grafts themselves may undergo minor degrees of resorption which causes the graft length to shorten or subside. This subsidence in turn is detrimental to the fusion process because the osteoblasts must now bridge an ever widening gap between host bone and graft. Ironically, rigid plating systems may actually work against the fusion process by holding host bone in a fixed position as subsidence occurs. To counteract this, many plating systems have resorted to semirigid systems that allow for screw and plate movement to counteract the effect of normal graft subsidence. That is, as the graft subsides, the screws above and below the graft are permitted to move via the force of gravity to allow continued bone graft apposition.

The trouble with most of these mechanisms is that they allow for too many degrees of movement in too many places. Whereas the only movement necessary to counteract subsidence is movement in a unidimensional plane, many existing plating mechanisms allow for movement of the screws in several planes, amounting in essence to putting in loose screws, which defeats the purpose of a true stabilizing plating system.

It would be desirable to have a plating mechanism which would provide the rigidity necessary to stabilize vertebral elements in appropriate alignment for fusion while simultaneously allowing for subsidence solely along the plane it would be expected to occur. This would be a clear advantage over the majority of plating systems which permit movement of component parts in so many dimensions that their value in providing stability and their utility in enhancing fusion is questioned. Additionally, by employing features that counteract subsidence through both active and passive modalities, fusion can be further enhanced.

SUMMARY OF THE INVENTION

It is an object of this invention to provide a spinal fusion plate that provides the desirable features of stabilizing grafted bone interfaces, for sufficient time that bony union can occur.

It is also the objective of this invention to provide for compensatory movement to counteract the effect of subsidence in a single plane. That is to say, that as a graft subsides through the normal course of healing or graft incorporation, the plate will allow for the loss of graft length or height while simultaneously preserving normal spinal alignment and the intended relationships of the integral components of graft and host bone.

A further objective of this invention is to provide for both active or passive compensatory movements that counteract the effects of subsidence such that bony fusion can be further enhanced.

To achieve these objectives, a curved metal frame is used, having roughly the curvature of the normal spinal at the intended site to be fused. Housed within the frame are plates provided with screw holes which can accept bone screws for affixing the plates to the vertebral elements in a rigid or semi-rigid fashion.

The plates are intimately retained in the rigid frame with a tongue and groove arrangement which allows the plates to slide vertically up or down, but prevents movement in all other directions. That is, the plates have a single degree of freedom (vertical) with respect to the frame. The plates cannot move if the spine is flexed, extended or rotated, however, if graft subsidence occurs, the plates can settle while maintaining constant graft/host bone surface apposition.

In an alternative form of the invention, a spring mechanism is employed to actively counteract that effect of subsidence rather than relying on purely passive (gravity operated) effects. Movements that retard healing or thwart normal alignment are thus inhibited, while movement (subsidence) that enhances bony union is facilitated. Allowing movement in only one dimension is superior to plate constructions that are essentially loose or semi-rigid and permit movement of component parts in planes not conducive to controlled healing. Spring modulation of the translation plates continuously maintains active graft/bone opposition to further mitigate against the deleterious effects of subsidence.

BRIEF DESCRIPTION OF THE DRAWINGS

In the accompanying drawings:

FIG. 1 a perspective view of a passive version a translation fusion plate device embodying the invention;

FIG. 2 is an anteroposterior view thereof;

FIG. 3 is an anteroposterior view thereof, illustrative plate movement;

FIG. 4 is a section taken on plane 4-4 in FIG. 2;

FIG. 5 is a section taken on plane 5-5 in FIG. 2;

FIG. 6 is an anteroposterior view showing the fusion plate relative to spinal vertebra;

FIG. 7 is a side view thereof; and

DESCRIPTION OF THE PREFERRED EMBODIMENTS

Figure 10:
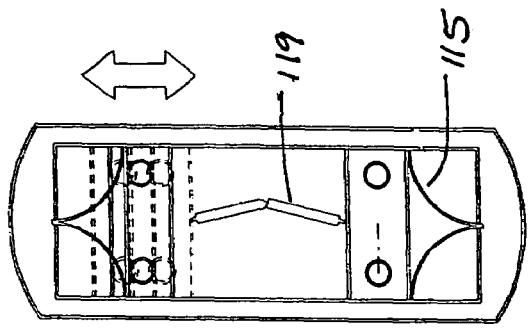
FIGS. 8-14 are corresponding views of active version of a translation fusion plate device embodying the invention.

FIGS. 1-5 depict the component parts of a passive version of a translation fusion plate device according to the invention.

The device 10 includes a rigid perimetral frame 12 and pair of translation plates 14. Bone screws 16 for fixing the translation plate 10 to a vertebral bone are also shown. Set screws 18 may be inserted in holes 20 to fixate the translation plate to the frame 12, should translation of one or more of the plates not be desired. As FIG. 5 shows, each plate 14 has at each end a tongue 22 which rides in a groove 24 in the facing longitudinal inner edge of the frame. Alternatively, the grooves could be formed on the plate ends and the tongues on the inner frame edges. Either way, the plate is retained within the frame opening while allowing for unidimensional translational movement, and no relative rotation between the plates, or between either plate and the frame.

FIGS. 6 and 7 shows the passive translation plate as it appears when attached to spinal vertebrae "V". Note the translation plate 14 sits within the frame 12 and is attached to the spinal vertebrae with the bone screws 16.

Figure 12:
Figure 9:
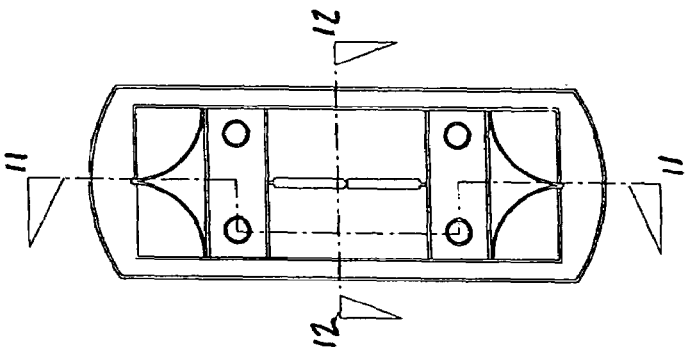
Figure 11:
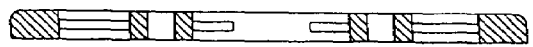
Figure 8:
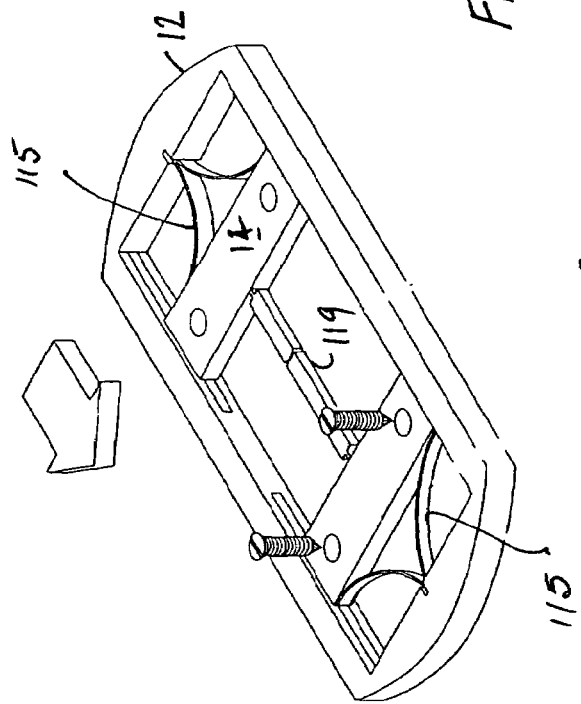
Figure 13:
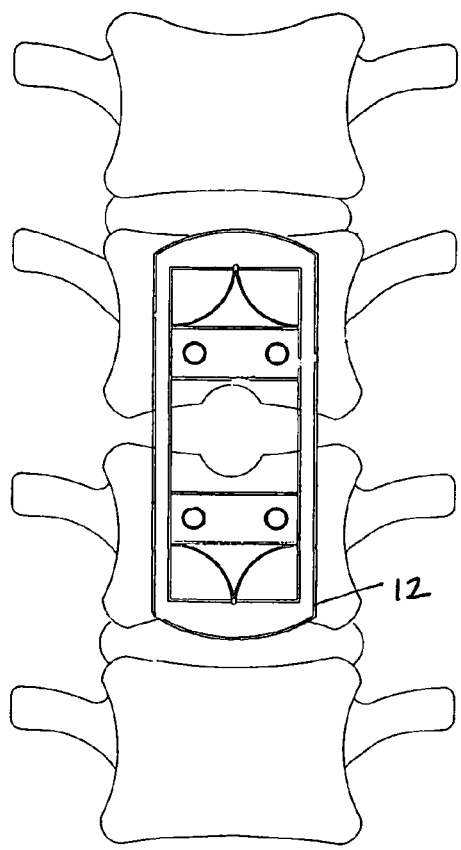
Figure 14:
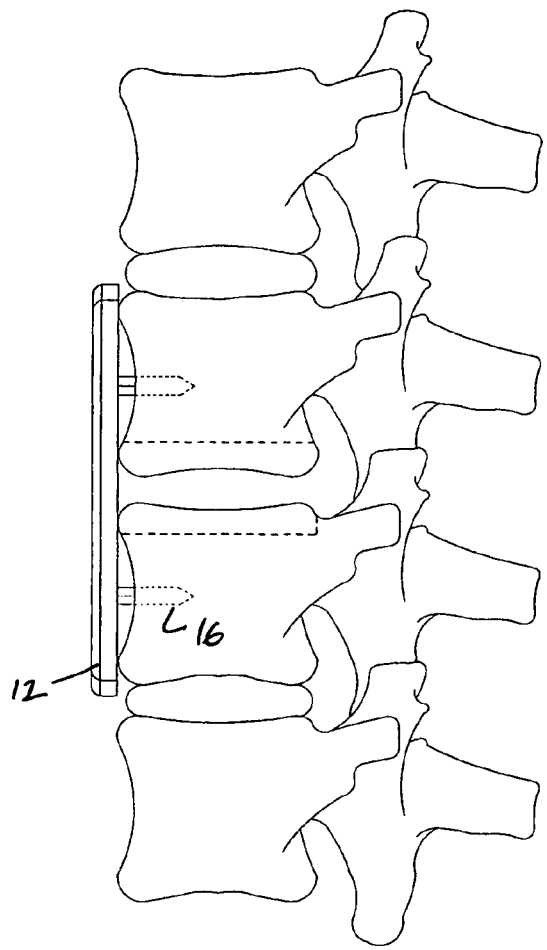

FIGS. 8-12 illustrate the component parts of the active version of the device. Here, the translation plates 14 are retained with the rigid frame 12, as before. Bone screws 16 which will fix the translation plate to vertebral bones are also shown. Leaf springs 115 are provided, one at either end between a respective plate and the top or bottom of the frame. The springs are designed so as to bias the translation plates toward one another. To facilitate handling of the device, the plates are initially held apart a predetermined distance by a break-away strut. The translation plates can move only after the break-away strut 119 is removed; thereafter, the translation plates 14 are biased toward one another by the leaf springs 115 in a controlled fashion, counteracting the effects of subsidence. The leaf springs could be replaced by coil springs, or some other suitable resilient element.

Inasmuch as the invention is subject to modification and variation, it is intended that the foregoing should be regarded as merely illustrative of the invention defined by the claims below.

I claim:

1. A spinal fusion plate device comprising
a rigid frame defining an opening,
two relatively movable plates, each plate being adapted to be connected to a respective vertebral body,
retaining structure for retaining both plates within said opening, said retaining structure permitting the plates to move in only a single dimension toward or away from one another, so as to mitigate the effect of subsidence and
means consisting of a pair of leaf springs for biasing the respective plates toward one another, to actively maintain continuous graft and host bone opposition as subsidence occurs,
wherein said springs are disposed at opposite ends of the frame, each said spring being disposed between the frame and a respective one of the plates and not between said plates.

2. The invention of claim 1, wherein each plate has means for receiving a pair of bone screws.

3. The invention of claim 1, wherein the retaining structure includes a tongue-and-groove arrangement.

4. The invention of claim 1, further comprising a breakable strut extending between said plates so as to hold the plates apart a predetermined distance until the strut is broken.

* * * * *